United States Patent
Jansson (10) Patent No.: US 9,962,476 B2
(45) Date of Patent: May 8, 2018

(54) INDIVIDUAL PUMP CALIBRATION FOR ULTRAFILTRATION CONTROL IN A DIALYSIS APPARATUS

(71) Applicant: GAMBRO LUNDIA AB, Lund (SE)

(72) Inventor: Olof Jansson, Vellinge (SE)

(73) Assignee: GAMBRO LUNDIA AB, Lund (SE)

( * ) Notice: Subject to any disclaimer, the term of this patent is extended or adjusted under 35 U.S.C. 154(b) by 202 days.

(21) Appl. No.: 14/901,881

(22) PCT Filed: Jul. 9, 2014

(86) PCT No.: PCT/EP2014/064743
§ 371 (c)(1),
(2) Date: Dec. 29, 2015

(87) PCT Pub. No.: WO2015/007595
PCT Pub. Date: Jan. 22, 2015

(65) Prior Publication Data
US 2016/0367743 A1 Dec. 22, 2016

(30) Foreign Application Priority Data
Jul. 15, 2013 (SE) ...................... 1350879

(51) Int. Cl.
*A61M 1/16* (2006.01)
*A61M 1/34* (2006.01)
(Continued)

(52) U.S. Cl.
CPC ............ *A61M 1/1615* (2014.02); *A61M 1/16* (2013.01); *A61M 1/165* (2014.02); *A61M 1/34* (2013.01);
(Continued)

(58) Field of Classification Search
None
See application file for complete search history.

(56) References Cited

U.S. PATENT DOCUMENTS 4,267,040 A   5/1981   Schal
4,275,726 A   6/1981   Schael
(Continued)

FOREIGN PATENT DOCUMENTS

CN   101347644   1/2009
CN   102389593   3/2012
(Continued)

OTHER PUBLICATIONS

International Search Report; PCT/EP2014/064763—dated Sep. 16, 2014—4 pages.
(Continued)

*Primary Examiner* — Chester T Barry
(74) *Attorney, Agent, or Firm* — K&L Gates LLP (57) ABSTRACT

A control unit (30) is arranged to control a dialysis fluid distribution system (12) comprising first and second volumetric pumps (P1, P2) arranged upstream and downstream of a dialyzer (13). The control unit (30) is operable in a calibration mode, to establish a bypass flow path that bypasses the dialyzer (13) and extends from the first pump (P1) to the second pump (P2) in fluid communication with a calibration chamber (26) and to operate the pumps (P1, P2) at different combinations of speeds that cause first and second changes in fluid level in the chamber (26). The first and second changes correspond to first and second known volumes in the chamber (26). The control unit (30) measures, by a level detector (28) in the chamber (26), first and second time periods for the first and second changes, and computes the stroke volumes of the pumps (P1, P2) as a function of the speeds of the pumps (P1, P2), the first and second time periods, and the first and second known volumes. By computing the stroke volumes, the control unit (30) is operable to achieve an accurate ultrafiltration (UF)

(Continued)

rate in the dialyzer (13) by controlling the relative speeds of the pumps (P1, P2).

21 Claims, 6 Drawing Sheets (51) Int. Cl.
F04B 49/06 (2006.01)
F04B 51/00 (2006.01)

(52) U.S. Cl.
CPC ......... *A61M 1/3413* (2013.01); *F04B 49/065* (2013.01); *F04B 51/00* (2013.01); *A61M 2205/12* (2013.01); *A61M 2205/3334* (2013.01); *A61M 2205/3389* (2013.01); *A61M 2205/3396* (2013.01); *A61M 2205/50* (2013.01); *A61M 2205/52* (2013.01); *A61M 2205/70* (2013.01); *A61M 2205/702* (2013.01)

(56) References Cited

U.S. PATENT DOCUMENTS

| | | |
|---|---|---|
| 4,334,988 A | 6/1982 | Milligan |
| 4,585,552 A | 4/1986 | Gummesson et al. |
| 4,747,950 A | 5/1988 | Guinn |
| 4,769,001 A | 9/1988 | Prince |
| 5,247,434 A | 9/1993 | Peterson |
| 5,954,951 A | 9/1999 | Nuccio |
| 6,331,252 B1 | 12/2001 | El Sayyid et al. |
| 6,691,047 B1 | 2/2004 | Fredericks |
| 2005/0006296 A1* | 1/2005 | Sullivan ............... A61M 1/1696 210/321.6 |
| 2007/0243990 A1 | 10/2007 | Kolenbrander et al. |
| 2008/0093276 A1 | 4/2008 | Roger et al. |
| 2008/0105600 A1 | 5/2008 | Connell et al. |
| 2009/0008331 A1 | 1/2009 | Wilt et al. |
| 2009/0124963 A1 | 5/2009 | Hogard et al. |
| 2009/0299273 A1* | 12/2009 | Lee .......................... A61M 1/28 604/29 |
| 2011/0132838 A1* | 6/2011 | Curtis ................... A61M 1/16 210/637 |
| 2012/0145615 A1 | 6/2012 | Rohde et al. |
| 2012/0193290 A1 | 8/2012 | Breuel et al. |
| 2012/0267309 A1 | 10/2012 | Peters et al. |
| 2012/0305090 A1* | 12/2012 | Bene ..................... A61M 1/342 137/2 |
| 2013/0020237 A1 | 1/2013 | Wilt et al. |

FOREIGN PATENT DOCUMENTS

| | | |
|---|---|---|
| DE | 69007342 | 9/1994 |
| DE | 10112848 | 9/2001 |
| WO | 9200768 | 1/1992 |
| WO | 2007118235 | 10/2007 |
| WO | 2013019994 | 2/2013 |

OTHER PUBLICATIONS

Written Opinion; PCT/EP2014/064763—dated Sep. 16, 2014—7 pages.
International Search Report; PCT/EP2014/064744; dated Sep. 16, 2014; 6 pages.
Written Opinion; PCT/EP2014/064744; dated Sep. 16, 2014; 8 pages.

* cited by examiner

INDIVIDUAL PUMP CALIBRATION FOR ULTRAFILTRATION CONTROL IN A DIALYSIS APPARATUS

CROSS-REFERENCE TO RELATED APPLICATIONS

The present application is a National Phase of International Application No. PCT/EP2014/064743, filed on Jul. 9, 2014, which claims priority to Sweden Patent Application No. 1350879-1, filed Jul. 15, 2013, the entire contents of each of which are incorporated herein by reference and relied upon.

TECHNICAL FIELD

The present invention relates to a technique for controlling ultrafiltration in connection with dialysis, and in particular to a technique for calibrating one or more volumetric pumps for pumping a dialysis fluid through a dialyzer in a dialysis apparatus.

BACKGROUND ART

In treating chronic renal failure, various methods of purification and treatment of blood with machinery are used to replace the function of a healthy kidney. Such methods aim at withdrawing fluid and removing substances from the blood, and they may also involve adding fluid and substances to the blood. Such purification and treatment may be performed by pumping a dialysis fluid through a blood filtration unit, commonly denoted a dialyzer, in which fluid and substances are transported over a semi-permeable membrane. Diffusive mass transport through the membrane is predominant in hemodialysis (HD), whereas hemofiltration (HF) uses mainly convective mass transport through the membrane. Hemodiafiltration (HDF) is a combination of the two methods.

The withdrawal of fluid in the dialyzer, also known as ultrafiltration, is given by the difference between the spent dialysis fluid pumped out of the dialyzer and the fresh dialysis fluid pumped into the dialyzer. Because of the large volume of dialysis fluid that is exposed to the membrane in the dialyzer during a dialysis treatment, there is a need for accurate control of the ultrafiltration. Taking hemodialysis as an example, typically about 200 liters of dialysis fluid are passed through the dialyzer during a treatment session. The target amount of ultrafiltrate during a treatment session is typically about 2 to 3 liters and may need to be controlled with a maximum deviation of the order of only 0.1 to 0.2 liter. Accordingly, in this example, ultrafiltration may need to be controlled with a maximum error of approximately 1:1000 in relation to the total flow of dialysis fluid.

There are different prior art techniques for achieving accurate control of ultrafiltration in a dialysis apparatus.

U.S. Pat. No. 4,267,040 discloses a dialysis apparatus having a passive balancing device. The balancing device consists of two chambers, each being subdivided by a displaceable element and having an inlet line for fresh dialysis fluid and an outlet line connected to a drain for spent dialysis fluid. Cutoff valves driven and switched by a control unit are arranged in the inlet and outlet lines. A pump is provided between the dialyzer and the balancing device to convey the dialysis fluid. The balancing device is operated in such a way that fresh dialysis fluid is supplied from a dialysis fluid source to the two balancing chambers in alternation through appropriate switching of the cutoff valves in the inlet lines. At the same time, fresh dialysis fluid is supplied from an already filled space of the other balance chamber to the dialyzer. The spent dialysis fluid from the dialyzer is pumped into the second space of the same balance chamber, from which the spent dialysis fluid then goes into an outlet. The part of the liquid circuit enclosed between the balancing device and the dialyzer behaves like a closed, constant-volume system. The ultrafiltration in the dialyzer, i.e. the amount of fluid that passes from the blood side to the dialysis fluid side of the dialyzer membrane, is controlled by a dedicated filtration pump which is connected for controlled removal of fluid from the system.

A dialysis apparatus equipped with this type of balancing device has a number of disadvantages. For one, the switching of the balancing chambers may produce audible noise to the discomfort of the patient undergoing dialysis and also the caretakers. Audible noise may be highly undesirable in a clinic setting as well as in a home setting. Further, the cutoff valves that control the switching will be subjected to significant mechanical load over time and may start to leak dialysis fluid as result of wear and fatigue. Any such leaks will produce errors in the resulting ultrafiltration. Still further, errors in the dedicated filtration pump will have a significant impact on the accuracy of the ultrafiltration, and it may be necessary to take measures to carefully control and supervise the operation of the filtration pump.

In this context, DE69007342 discloses a technique for calibrating a filtration pump, which is a volumetric pump that has either a rotor or a diaphragm for displacing the dialysis fluid. The pump is equipped with a pulse generator which emits pulses that represent a certain angle of rotation of the rotor or a certain displacement of the diaphragm and correspond to a certain quantity of dialysis fluid. During regular operation, the flow rate of the filtration pump is determined by dead reckoning, i.e. by counting the number of pulses emitted and applying a known correspondence between the number of pulses and the quantity of liquid pumped. This correspondence is determined in a calibration procedure, in which the pumped liquid is switched into a reservoir of exactly known capacity. By counting the number of pulses emitted in order to fill the reservoir, the exact correspondence between the number of pulses emitted and the quantity of liquid pumped can be determined.

The prior art also comprises U.S. Pat. No. 4,747,950 which is designed to balance the flow of dialysis fluid into the dialyzer, generated by an upstream pump, with the flow of dialysis fluid out of the dialyzer, generated by a downstream pump, and to achieve ultrafiltration by withdrawing a controlled amount of dialysis fluid from a location either upstream or downstream of the dialyzer. The disclosed dialysis fluid supply system contains a large number of pumps, in addition to the upstream and downstream pumps, and involves a complex distribution of dialysis fluid between and within different receptacles in the system. To ensure a balanced flow, a calibration procedure is implemented, in which the dialyzer is temporarily by-passed such that the dialysis fluid is pumped from the upstream pump through a calibration chamber to the downstream pump. The calibration chamber has a sight tube allowing the level of dialysis fluid to be visually inspected. The flow rate of the upstream pump is controlled in relation to the flow rate of the downstream pump until the level of dialysis fluid remains at a constant level in the sight tube.

Other techniques for ultrafiltration control by balancing the flow rates of fresh and spent dialysis fluid are e.g. known from US2012/0193290, US2011/0132838, US2008/0105600, US2002/0088752, US2012/0279910 and US2010/0016777.

Another approach to control the ultrafiltration during dialysis is to install one or more pumps upstream of the dialyzer and one or more pumps downstream the dialyzer in the dialysis fluid supply system and to relatively control the flow rates of the upstream and downstream pumps to achieve a desired ultrafiltration rate. This type of control requires accurate measurements of the flow rates of dialysis fluid into and out of the dialyzer, and one or more advanced flow meters are installed in the dialysis fluid supply system to provide this information. An example of a flow meter capable of measuring the difference between the dialysis fluid flows into and out of the dialyzer is known from U.S. Pat. No. 4,585,552. A dialysis apparatus based on this approach may produce significantly less audible noise than a dialysis device with a balancing device. Further, since the ultrafiltration is controlled based on the readings of one or more flow meters, ultrafiltration may be largely unaffected by leaks in the dialysis fluid supply system, as long as the flow meter(s) operate correctly. However, flow meters with the required accuracy and precision may be quite costly and complex. It is also vital that the flow meters operate correctly over a long time of use. Techniques for calibrating the flow meters in this context are e.g. known from U.S. Pat. No. 6,331,252 and US2012/0145615.

The prior art also comprises US2007/0243990 which is unrelated to ultrafiltration control and discloses an apheresis system in which blood is removed from a donor, directed to a blood component separation device, such as a centrifuge, which collects one or more blood components (e.g. red blood cells, white blood cells, platelets or plasma), whereupon the remainder is returned to the donor. US2007/0243990 proposes a calibration procedure for relatively calibrating pairs of pumps in the apheresis system. During the calibration procedure, the pumps are alternately activated so that one pump is operated to increase the fluid level in a reservoir from an initial level, and then the other pump is operated to decrease the fluid level back to the initial level in the reservoir. A pump volume ratio between the pumps is given by the number of strokes performed by the respective pump while filling and emptying the reservoir. The pump volume ratio is stated to be useful for increasing the effectiveness and efficiency of the donation process. Another technique for relative pump calibration in the context of apheresis for blood plasma filtering and/or platelet separation is known from U.S. Pat. No. 4,769,001.

SUMMARY

It is an objective of the invention to at least partly overcome one or more limitations of the prior art.

One objective is to provide an alternative technique of controlling ultrafiltration in a dialysis apparatus.

Another objective is to provide a simple, accurate and robust technique of controlling ultrafiltration in a dialysis apparatus.

A still further objective is to enable a silent dialysis apparatus.

One or more of these objectives, as well as further objectives that may appear from the description below, are at least partly achieved by a dialysis apparatus, a method of calibrating a dialysis fluid distribution system, a computer-readable medium, and control units according to the independent claims, embodiments thereof being defined by the dependent claims.

A first aspect of the invention is a dialysis apparatus, comprising: a dialyzer; a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber; a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid; wherein the control unit is configured to, in a calibration mode, perform a first and second measurement procedure while operating the dialysis fluid distribution system to establish the bypass flow path; wherein the first measurement procedure comprises: controlling the first and second pumps to operate at a first combination of frequencies that results in a first flow rate difference between the flow rates generated by the first and second pumps, and measuring, by the fluid level detector, a first time period corresponding to a first change in dialysis fluid level in the calibration chamber as a result of the first flow rate difference, the first change in dialysis fluid level corresponding to a first known volume in the calibration chamber; wherein the second measurement procedure comprises: controlling the first and second pumps to operate at a second combination of frequencies that differs from the first combination of frequencies and results in a second flow rate difference between the flow rates generated by the first and second pumps, and measuring, by the fluid level detector, a second time period corresponding to a second change in dialysis fluid level in the calibration chamber as a result of the second flow rate difference, the second change in dialysis fluid level corresponding to a second known volume in the calibration chamber; and wherein the control unit is further configured to compute at least one of the stroke volumes of the first and second pumps as a function of the first and second combinations of frequencies, the first and second time periods, and the first and second known volumes.

The first aspect provides a technique for calibrating one or more of the pumps in the dialysis fluid distribution system, in the sense that the actual stroke volume of the pump is estimated. The calibration is simple to implement, since it only involves establishing the bypass flow path, and then controlling the pumps to operate at different combinations of frequencies while monitoring the changes in fluid level in the calibration chamber. The pumps are volumetric pumps, which are configured to generate a respective flow rate by repeatedly discharging, at a respective operating frequency, a respective stroke volume of dialysis fluid. Thus, if the stroke volume is known with sufficient accuracy, the pump may be controlled to generate an accurate flow rate of dialysis fluid. Thus, in contrast to prior art techniques for controlling ultrafiltration, the first aspect makes it possible to directly and accurately control the flow rate of dialysis fluid that is generated by an individual pump in the dialysis fluid distribution system. This means that it is possible to dispense with highly advanced, complex and costly flow meters as well as noisy, complex and costly balancing devices. Thereby, the first aspect enables a simplification in the design of the dialysis apparatus. In the absence of balancing chambers and advanced flow meters, the robustness of the dialysis apparatus may also be increased. Further, the dialysis apparatus of the first aspect may be switched to the calibration mode at any time to re-calibrate the pump or pumps. Thus, by the first aspect, the dialysis apparatus may compensate for changes or drifts in the stroke volume of the pumps. In the absence of a balancing device, the dialysis apparatus may be designed to produce significantly less audible noise.

It should be emphasized, though, that the present invention may be combined with both a flow meter for measuring the flow rate of dialysis fluid and a balancing device for balancing the flows of dialysis fluid to and from the dialyzer, if desired.

The dialysis apparatus of the first aspect may be operated to control the ultrafiltration in the dialyzer by directly setting the operating frequencies of the pumps, which are located upstream and downstream of the dialyzer in the main flow path, such that the difference between the flow rates generated by the pumps equals the desired ultrafiltration rate. Alternatively, the dialysis apparatus of the first aspect may be operated to control the ultrafiltration in the dialyzer by setting the operating frequencies of the pumps such that their flow rates are balanced, and by controlling a dedicated filtration pump, which is connected to the main flow path downstream of the dialyzer, to generate a flow rate equal to the desired ultrafiltration rate. In one embodiment, the control unit is further configured to, in the calibration mode, store the stroke volume(s) computed in the calibration mode in an electronic memory for subsequent retrieval by the control unit in the treatment mode.

As used herein, "upstream" and "downstream" refers to a direction in relation to the flow of dialysis fluid in the main flow path.

In one embodiment, the first and second pumps are positive displacement pumps, and the flow rates of dialysis fluid generated by the first and second pumps are given by the respective frequency multiplied by the respective stroke volume.

In one embodiment, the function is obtained by solving a system of equations that equals the first known volume to an accumulated difference between the flow rates generated by the first and second pumps during the first time period, and that equals the second known volume to an accumulated difference between the flow rates generated by the first and second pumps during the second time period.

In one embodiment, the control unit is configured to set the first and second combinations of frequencies such that the first change is an increase in dialysis fluid level in the calibration chamber, and the second change is a decrease in dialysis fluid level in the calibration chamber.

In one embodiment, the first change is from a first level to a second level in the calibration chamber, and the second change is from the second level to the first level in the calibration chamber.

In one embodiment, the control unit is configured to, in the first measurement procedure, set the first and second pumps to fixed first and second frequencies, and, in the second measurement phase, set the first and second pumps to fixed third and fourth frequencies.

In one embodiment, the function is given by:

$$\begin{bmatrix} S1 \\ S2 \end{bmatrix} = \frac{1}{n1 \cdot n4 - n2 \cdot n3} \cdot \begin{bmatrix} n4 & -n2 \\ n3 & -n1 \end{bmatrix} \cdot \begin{bmatrix} V1/t1 \\ V2/t2 \end{bmatrix}$$

where S1 is the stroke volume of the first pump, S2 is the stroke volume of the second pump, n1 is the first frequency, n2 is the second frequency, n3 is the third frequency, n4 is the fourth frequency, V1 is the first known volume corresponding to the first change in dialysis fluid level, V2 is the second known volume corresponding to the second change in dialysis fluid level, t1 is the first time period, and t2 is the second time period, wherein V1 is positive for an increase in dialysis fluid level and negative for a decrease in dialysis fluid level and V2 is positive for a decrease in dialysis fluid level and negative for an increase in dialysis fluid level.

In one embodiment, each of the first and second pumps is one of a diaphragm pump and a piston pump.

In one embodiment, the control unit is further operable in a treatment mode, wherein the control unit is configured to, in the treatment mode, operate the dialysis fluid distribution system to establish the main flow path and control the frequencies of the first and second pumps, based on the stroke volume(s) computed in the calibration mode, so as to achieve a predefined ultrafiltration rate in the dialyzer. In one implementation, the predefined ultrafiltration rate is achieved by setting the frequencies of the first and second pumps to achieve a predefined difference between the flow rates generated by the first and second pumps.

In one embodiment, the control unit is configured to, in the treatment mode, receive a set value for the flow rate of one of the first and second pumps, and compute, by applying the corresponding stroke volume computed in the calibration mode, the frequency of said one of the first and second pumps to achieve the set value. In one implementation, said one of the first and second pumps is the first pump, which is arranged upstream of the dialyzer in the main flow path.

In one embodiment, the control unit is configured to, in the treatment mode, receive a set value for the ultrafiltration rate in the dialyzer, compute an ultrafiltration control flow rate for the other of the first and second pumps based on the set values for the flow rate and the ultrafiltration rate, and compute, by applying the corresponding stroke volume computed in the calibration mode, the frequency of said other of the first and second pumps to achieve the ultrafiltration control flow rate.

Generally, in all embodiments disclosed herein, it may be advantageous for both of the first and second pumps to be active, i.e. to be controlled to operate at non-zero frequencies, during at least part of the first and second measurement procedures, and preferably during the entire first and second measurement procedures. This will increase the length of the first and second time periods, and thereby potentially improve the accuracy of the computed stroke volume(s). Furthermore, for reasons of ultrafiltration accuracy, it may be advantageous to operate the first and second pumps during the calibration mode at frequencies near, or at least not distant from, the operating frequencies that are to be used for the first and second pumps during the treatment mode to achieve the above-mentioned flow rate and ultrafiltration rate.

A second aspect of the invention is a method of calibrating a dialysis fluid distribution system that comprises first and second pumps which are connected upstream and downstream of a dialyzer to pump a dialysis fluid through the dialyzer, wherein the first and second pumps are configured to generate a respective flow rate by repeatedly discharging, at a respective frequency, a respective stroke volume of the dialysis fluid. The method comprises: operating the dialysis fluid distribution system to establish a bypass flow path, which bypasses the dialyzer and extends from the first pump to the second pump in fluid communication with a calibration chamber; controlling the first and second pumps to operate at a first combination of frequencies that results in a first flow rate difference between the flow rates generated by the first and second pumps; measuring a first time period corresponding to a first change in dialysis fluid level in the calibration chamber as a result of the first flow rate difference, the first change in dialysis fluid level corresponding to a first known volume in the calibration chamber; controlling the first and second pumps to operate at a second combination of frequencies that differs from the first combination of frequencies and results in a second flow rate difference between the flow rates generated by the first and second pumps; measuring a second time period corresponding to a second change in dialysis fluid level in the calibration chamber as a result of the second flow rate difference, the second change in dialysis fluid level corresponding to a second known volume in the calibration chamber; and computing at least one of the stroke volumes of the first and second pumps as a function of the first and second combinations of frequencies, the first and second time periods, and the first and second known volumes.

A third aspect of the invention is a computer-readable medium comprising program instructions which, when executed by a processing unit, is adapted to carry out the method of the second aspect.

Fourth and fifth aspects of the invention concern a control unit for a dialysis fluid distribution system arranged in a dialysis apparatus to pump a dialysis fluid through a dialyzer. The dialysis fluid distribution system comprises first and second pumps which are connected upstream and downstream of the dialyzer to pump a dialysis fluid through the dialyzer, and are configured to generate a respective flow rate by repeatedly discharging, at a respective frequency, a respective stroke volume of the dialysis fluid.

The control unit of the fourth aspect comprises: a signal communication interface for connection to the dialysis fluid distribution system; and a signal processor which is configured to, via the signal communication interface: operate the dialysis fluid distribution system to establish a bypass flow path, which bypasses the dialyzer and extends from the first pump to the second pump in fluid communication with a calibration chamber; control the first and second pumps to operate at a first combination of frequencies that results in a first flow rate difference between the flow rates generated by the first and second pumps; measure, by a fluid level detector for sensing a level of dialysis fluid in the calibration chamber, a first time period corresponding to a first change in dialysis fluid level in the calibration chamber as a result of the first flow rate difference, the first change in dialysis fluid level corresponding to a first known volume in the calibration chamber; control the first and second pumps to operate at a second combination of frequencies that differs from the first combination of frequencies and results in a second flow rate difference between the flow rates generated by the first and second pumps; and measure, by the fluid level detector, a second time period corresponding to a second change in dialysis fluid level in the calibration chamber as a result of the second flow rate difference, the second change in dialysis fluid level corresponding to a second known volume in the calibration chamber. The signal processor is further configured to compute at least one of the stroke volumes of the first and second pumps as a function of the first and second combinations of frequencies, the first and second time periods, and the first and second known volumes.

The control unit of the fifth aspect comprises: means for operating the dialysis fluid distribution system to establish a bypass flow path, which bypasses the dialyzer and extends from the first pump to the second pump in fluid communication with a calibration chamber; means for controlling the first and second pumps to operate at a first combination of frequencies that results in a first flow rate difference between the flow rates generated by the first and second pumps; means for measuring a first time period corresponding to a first change in dialysis fluid level in the calibration chamber as a result of the first flow rate difference, the first change in dialysis fluid level corresponding to a first known volume in the calibration chamber; means for controlling the first and second pumps to operate at a second combination of frequencies that differs from the first combination of frequencies and results in a second flow rate difference between the flow rates generated by the first and second pumps; means for measuring a second time period corresponding to a second change in dialysis fluid level in the calibration chamber as a result of the second flow rate difference, the second change in dialysis fluid level corresponding to a second known volume in the calibration chamber; and means for computing at least one of the stroke volumes of the first and second pumps as a function of the first and second combinations of frequencies, the first and second time periods, and the first and second known volumes.

Any one of the above-identified embodiments of the first aspect may be adapted and implemented as an embodiment of the second to fifth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings. Throughout the description, the same reference numerals are used to identify corresponding elements.

DETAILED DESCRIPTION OF EXAMPLE EMBODIMENTS

Figure 1:
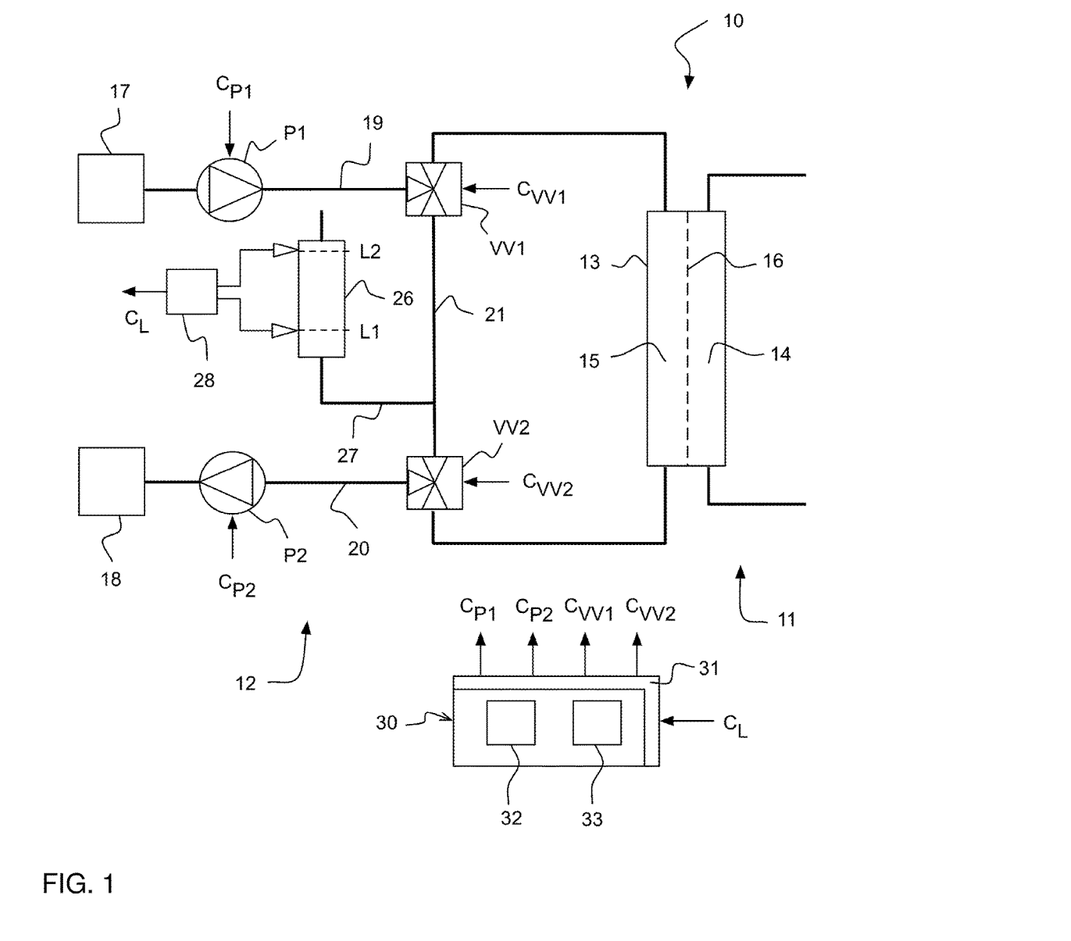
FIG. 1 is a block diagram of a system for ultrafiltration according to an embodiment.

FIG. 1 illustrates an embodiment of a system 10 for ultrafiltration. The system 10 may be included in a dialysis apparatus. It is understood that only components relevant to the following description are represented in FIG. 1, with other components being well within the purview of one skilled in the art to ascertain. The system 10 comprises a blood circuit 11, a dialysis fluid circuit 12 and a dialyzer 13. The dialyzer 13 is a blood filtration unit that generally has a blood side 14 and an dialysis fluid side 15 separated by a semipermeable membrane 16. The blood circuit 11 is connected to an inlet and an outlet of the blood side 14. One or more pumps (not shown) are arranged in the blood circuit 11 to pump blood from a source (not shown) through the dialyzer 13 to a receptacle (not shown). The blood may e.g. be pumped from the cardiovascular system of a subject and back to the subject, as is well-known in the art. The dialyzer 13 may be any of the well-known dialyzers useful for hemodialysis, such as a coil dialyzer, a parallel plate dialyzer, a hollow fiber dialyzer, etc.

The dialysis fluid circuit 12 extends from a source 17 of fresh dialysis fluid to a receptacle or drain 18 for spent dialysis fluid. The dialysis fluid circuit 12 includes an arrangement of fluid lines that define an inlet conduit 19 connected to an inlet of the dialysis fluid side 15 of the dialyzer 13, an outlet conduit 20 connected to an outlet of the dialysis fluid side 15 of the dialyzer 13, and a bypass conduit 21 that extends between the inlet and outlet conduits 19, 20. A first pump P1 ("upstream pump") is arranged in the inlet conduit 19 to pump dialysis fluid from the source 17, and a second pump P2 ("downstream pump") is arranged in the outlet conduit 20 to pump dialysis fluid towards the receptacle 18. A first and a second three-way valve VV1, VV2 are arranged in the inlet conduit 19 and the outlet conduit 20, respectively, and are connected to the bypass conduit 21. The first valve VV1 is operable to establish fluid communication either between the first pump P1 and the dialyzer 13, or between the first pump P1 and the bypass conduit 21. The second valve VV2 is operable to establish fluid communication either between the dialyzer and the second pump P2, or between the bypass conduit 21 and the second pump P2. A calibration chamber 26 is arranged in fluid communication with the bypass conduit 21 via a connecting conduit 27. A level detector 28 is installed to generate a sensor signal $C_L$ which is indicative of at least two different levels of fluid, depicted as a lower level L1 and an upper level L2, in the calibration chamber 26. The level detector 28 may be of any conventional type that allows multi-point or continuous level detection, such as an ultrasonic detector, an optical detector, a capacitive detector, a microwave sensor, a hydrostatic sensor, a magnetic float detector, etc.

The system 10 further includes an electronic control unit 30 which has a signal communication interface 31 for electrical connection to electrically responsive components in the dialysis fluid circuit 12. Specifically, the control unit 30 is operable to receive the sensor signal $C_L$ from the level detector 28 and to generate and output control signals $C_{P1}$, $C_{P2}$ for controlling the operation of the pumps P1, P2 and control signals $C_{VV1}$, $C_{VV2}$ for controlling the switching of the valves VV1, VV2. The control unit 30 may implement further functions of the dialysis apparatus and may be included as a part of a control system for the dialysis apparatus. The control unit 30 may be a computer, or a similar data processing device, with adequate hardware for acquiring, processing and generating signals in accordance with different embodiments of the invention. Embodiments of the invention may be implemented by software instructions that are supplied on a computer-readable medium for execution by a processor 32 in conjunction with an electronic memory 33 in the device 30, as indicated in FIG. 1. The computer-readable medium may be a tangible product (e.g. magnetic medium, optical disk, read-only memory, flash memory, etc.) or a propagating signal.

The system 10 is operable in a treatment mode, in which the control unit 30 controls the dialysis fluid circuit 12 to generate a flow of dialysis fluid through the dialysis fluid side 15 of the dialyzer 13. During the treatment mode, the pumps P1, P2 are set to generate different flow rates, such that the flow rate of the downstream pump P2 exceeds the flow rate of the upstream pump P1 by the desired ultrafiltration rate in the dialyzer 13. As explained in the Background section, the ultrafiltration rate (or UF rate) is the rate of fluid removal from the blood that takes place in the dialyzer 13. In blood treatment, UF generally denotes a process of removing water from blood plasma. The blood is passed on the blood side 14 of the dialyzer 13, and a gradient of pressure is created through the semipermeable membrane 16 by the difference in flow rates between the pumps P1, P2. The pressure gradient forces fluid through the pores of the membrane 16. The pores filter electrolytes and small and middle sized molecules (up to 20,000 to 30,000 daltons) from the blood plasma.

The pumps P1, P2 are "volumetric pumps", which means that each pump is configured to generate a given flow rate by repeatedly discharging a respective stroke volume of dialysis fluid. Volumetric pumps are well-known per se and are also referred to as positive displacement pumps. A volumetric pump is configured to drive a fluid by trapping a fixed and well-defined volume of the fluid in a pump chamber and by forcing (displacing) that trapped volume through a pump outlet by a movable pumping element, e.g. a piston or a diaphragm. Volumetric pumps that may be used in the embodiment of FIG. 1 include reciprocating pumps such as piston pumps and diaphragm pumps. One characteristic of volumetric pumps is that they have a well-defined stroke volume, and that the flow rate of a volumetric pump is controlled via the frequency of the pump, i.e. the frequency of the stroke volumes that are discharged by the pump. In the following, the "speed" of a pump is synonymous with the frequency of stroke volumes.

The volumetric pumps are manufactured with a nominal stroke volume. However, the actual stroke volume of an individual pump may differ from the nominal stroke volume due to tolerances in manufacture and assembly of the pump. Further, the stroke volume may change during operation of the pump, e.g. due to build-up of deposits or contaminations in the pump chamber or due to wear of the pumping element or the pump chamber. Depending on the type of pump, the stroke volume may also vary depending on the fluid pressure at the inlet and/or outlet of the pump.

Even small differences between the actual and nominal stroke volumes of the pumps P1, P2 may lead to a large deviation between the desired UF rate and the actual UF rate that is generated by the flow rate difference between the pumps P1, P2. This sensitivity will be illustrated by reference to a numeric example. Assume that the pumps P1, P2 are identical to the degree that their nominal stroke volume is 3.8 ml but that their actual stroke volumes deviate by −1% and +1%, respectively, from the nominal stroke volume. Also assume that the set value for the inlet flow of dialysis fluid to the dialyzer is 500 ml/min and that the desired UF rate is 500 ml/h. Using the nominal stroke volumes to achieve this UF rate, the speed of pump P1 is set to 500/3.8=131.58 strokes/min and the speed of pump P2 is set to (500+500/60)/3.8=133.77 strokes/min. However, based on the actual stroke volumes, the pump P1 will generate a flow rate of 131.58*3.8*1.01=505.00 ml/min and pump P2 will generate a flow rate of 133.77*3.8*0.99=503.25 ml/min. Thus, the actual UF rate is (503.25−505.00)*60=−105 ml/h. This means that instead of removing 500 ml fluid per hour from the blood, the system will pump 105 ml fluid per hour into the blood.

It is realized that proper control of the UF rate may require the pumps P1, P2 to be manufactured with very tight tolerances so that the actual stroke volumes closely correspond to the nominal stroke volumes. To overcome this drawback, embodiments of the invention take the approach of calibrating the pumps P1, P2 before or even during ongoing blood processing. To this end, the system 10 is configured to be operable in a calibration mode, in which the actual stroke volumes of the pumps P1, P2 are calculated or estimated by clever control of the pumps P1, P2 and use of the calibration chamber 26. The calibration mode is implemented by the control unit 30, which generates dedicated control signals $C_{P1}$, $C_{P2}$, $C_{VV1}$, $C_{VV2}$ and processes the sensor signal $C_L$ for calculation of the actual stroke volumes. In the following, the actual stroke volumes of the pumps P1, P2 are represented as S1, S2, respectively.

Figure 2:
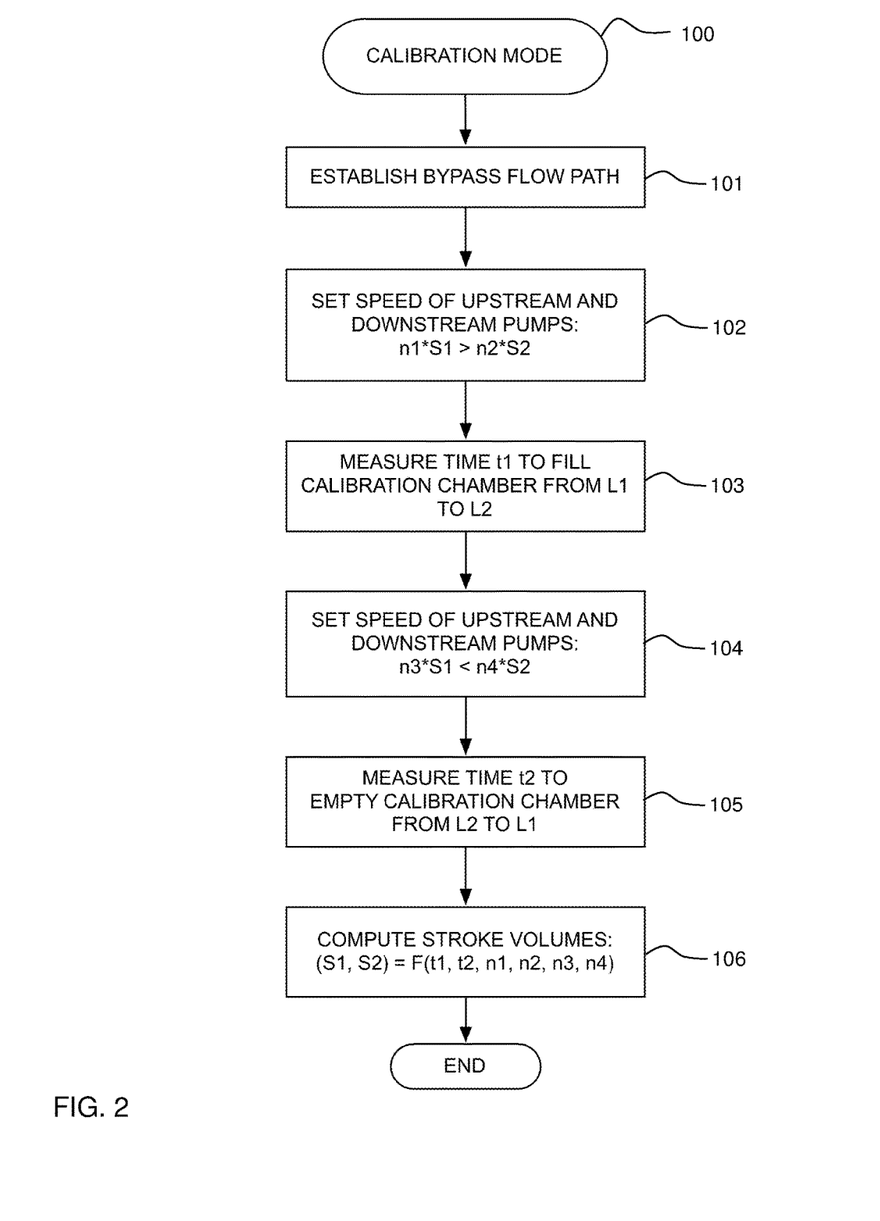
FIG. 2 is a flow chart of a calibration mode executed by a control unit in the system of FIG. 1.
Figure 3A:
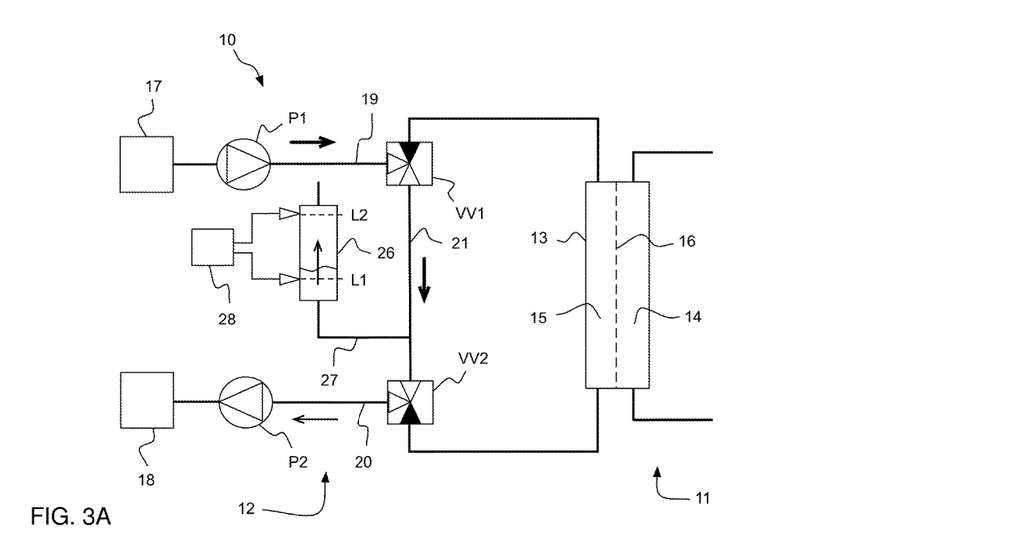
FIGS. 3A-3B illustrate the operation of the system in FIG. 1 in two different measurement phases during the calibration mode in FIG. 2.
Figure 3B:
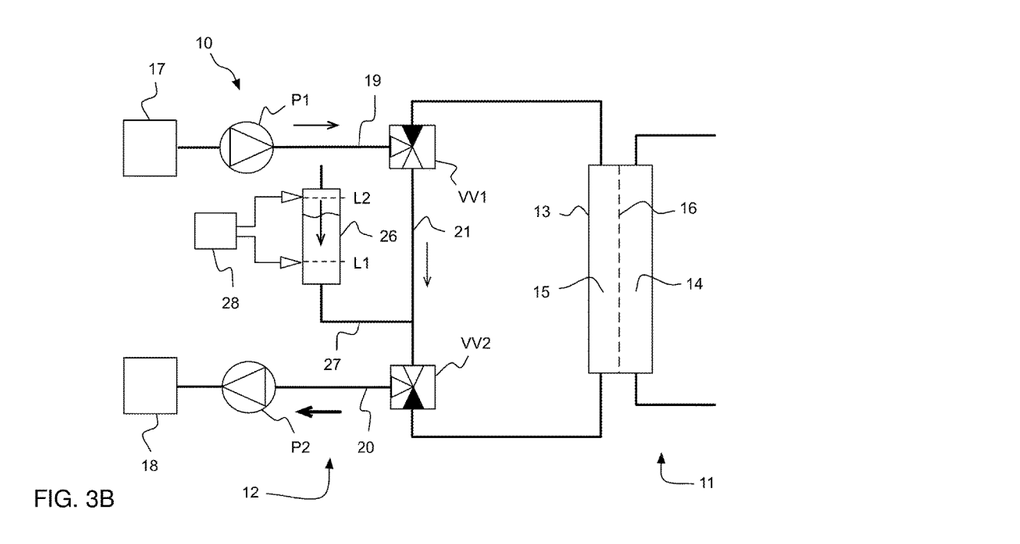

An embodiment of the calibration mode 100 is represented in the flow chart of FIG. 2 and will be discussed below with further reference to FIGS. 3A-3B. In a first step 101, the valves VV1, VV2 are controlled to establish a direct flow path between the pumps P1, P2, i.e. a flow path that bypasses the dialyzer 12. This bypass flow path is also in fluid communication with the calibration chamber 26. In the example of FIG. 3A, the valves VV1, VV2 are controlled to establish fluid communication between the inlet and outlet conduits 19, 20 via the bypass conduit 21, while closing off the fluid communication to and from the dialyzer 13. Thereby, all of the fresh dialysis fluid will be pumped from the source 17 through the bypass conduit 21 to the receptacle 18. In FIGS. 3A-3B, a closed valve passage is represented by a filled triangle and an open valve passage is represented by an open triangle. In step 102, the pumps P1, P2 are set to a respective speed n1, n2 such that the flow rate generated by pump P1 exceeds the flow rate generated by pump P2. The speed settings n1, n2 may be pre-defined and known to produce a difference in flow rates between the pumps P1, P2. When the pumps P1, P2 are operated at speeds n1, n2, a surplus of dialysis fluid will be pushed into the calibration chamber 26 via the connecting conduit 27 and the fluid level in the chamber 26 will increase, as indicated by the upward arrow in the chamber 26 in FIG. 3A. Thus, step 102 controls the system 10 to fill the chamber 26 from L1 to L2. In step 103, while the pumps operate at speeds n1, n2, the sensor signal $C_L$ is monitored to measure the time t1 ("filling time") required to move the fluid level from L1 to L2 in the calibration chamber 26. When the fluid level reaches or exceeds level L2, the pumps P1, P2 are stopped. In step 104, the pumps P1, P2 are set to a respective speed n3, n4 such that the flow rate generated by pump P2 exceeds the flow rate generated by pump P1. When the pumps P1, P2 are operated at speeds n3, n4, dialysis fluid will be drawn out of the calibration chamber 26 via the connecting conduit 27 and the fluid level in the chamber 26 will decrease, as indicated by the downward arrow in the chamber 26 in FIG. 3B. Thus, step 104 controls the system 10 to empty the chamber 26 from L2 to L1. In step 105, while the pumps operate at speeds n3, n4, the sensor signal $C_L$ is monitored to measure the time t2 ("emptying time") required to move the fluid level from L2 to L1 in the calibration chamber 26. When the fluid level reaches or falls below level L1, the pumps P1, P2 are stopped. In step 106, actual stroke volumes S1, S2 are computed as a function of the measured filling and emptying times t1, t2 and the set speeds n1, n2, n3, n4. The actual stroke volumes are then stored in the electronic memory (33 in FIG. 1) for subsequent retrieval when the system 10 enters a treatment mode (see below). The basis for the calculations in step 106 is that the volume of fluid between the levels L1, L2 in the chamber 26 is known. This volume, denoted V, may e.g. be measured in a separate calibration step before installing the calibration chamber 26 in the system 10. Alternatively, the chamber 26 may be designed to have a nominal volume between the levels L1, L2 and this nominal volume may be used as volume V. The following system of equations is obtained:

$$\begin{cases} (n1 \cdot S1 - n2 \cdot S2) \cdot t1 = V \\ (n3 \cdot S1 - n4 \cdot S2) \cdot t2 = -V \end{cases}$$

where V is the volume of fluid between L1 and L2. A function F1 for the actual stroke volumes S1, S2 is obtained by solving the above system of equations:

$$F1: \begin{cases} S1 = \dfrac{V}{n1 \cdot n4 - n2 \cdot n3} \cdot \left(\dfrac{n4}{t1} - \dfrac{n2}{t2}\right) \\ S2 = \dfrac{V}{n1 \cdot n4 - n2 \cdot n3} \cdot \left(\dfrac{n3}{t1} - \dfrac{n1}{t2}\right) \end{cases}$$

The set values n1, n2, n3, n4 for the pump speeds and the volume V may be pre-defined entities which are stored in the electronic memory 33 and retrieved by the processor 32 (FIG. 1) during execution of the calibration mode.

It should be noted that the embodiment presented in FIG. 3 is merely given as an example. For example, it is not necessary to stop the pumps P1, P2 at the end of steps 103 and 105. Instead, the pumps P1, P2 may be kept running while the speed of one or both pumps P1, P2 is changed so as to achieve a desired movement, or lack of movement, of the fluid level in the calibration chamber. Furthermore, it is not necessary that the filling and emptying times t1, t2 are measured with respect to the same levels in the chamber 26. Instead, different start and end levels may be used in step 103 and step 105. However, the use of only two levels may lower the requirements of the level detector 28, since it only needs be configured for detection of two fluid levels. The use of the same two only levels in step 103 and step 105, as shown in FIGS. 3A-3B, may also make it possible to optimize the design of the chamber 26 to improve the accuracy and precision of the level detection. An example of such an optimized chamber is presented below with reference to FIG. 6. Further, it is not necessary to implement step 102 to fill the chamber 26 by increasing the fluid level and step 104 to empty the chamber by decreasing the fluid level. Of course, it is equally possible to reverse the order between filling and emptying of the chamber 26, provided that the chamber 26 is properly filled at the start of step 102. However, it is also possible to implement both of steps 102 and 104 to either decrease or increase the fluid level in the chamber 26 from a start level to an end level. For example, the fluid level may be repeatedly reciprocated in the chamber 26 in a sequence of filling and emptying phases, by proper control of the relative speeds of the pumps P1, P2, and the measurement steps 103 and 105 may be performed during two filling phases or two emptying phases.

In a more generalized embodiment, steps 102-103 define a first measurement phase or procedure in which the pumps P1, P2 are controlled to operate at a first combination of speeds n1, n2 that result in a first flow rate difference that cause a first change (increase or decrease) of the fluid level in the calibration chamber 26 during a first time period t1, and steps 104-105 define a second measurement phase or procedure in which the pumps P1, P2 are controlled to operate at a second combination of speeds n3, n4 that result in a second flow rate difference that cause a second change (increase or decrease) of the fluid level in the calibration chamber 26 during a second time period t2. The first and second changes in fluid level correspond to first and second known volumes in the calibration chamber 26. If these volumes are designated V1 and V2, where V1 is defined to be positive for an increase in fluid level and negative for a decrease in fluid level and V2 is defined to be positive for a decrease in fluid level and negative for an increase in fluid level, the function F1 may be generalized into:

$$F2: \begin{bmatrix} S1 \\ S2 \end{bmatrix} = \frac{1}{n1 \cdot n4 - n2 \cdot n3} \cdot \begin{bmatrix} n4 & -n2 \\ n3 & -n1 \end{bmatrix} \cdot \begin{bmatrix} V1/t1 \\ V2/t2 \end{bmatrix}$$

Function F2, like function F1, is obtained by solving a system of equations that equals the volume V1 to an accumulated difference between the flow rates generated by the pumps P1, P2 during the first measurement phase, and that equals the volume V2 to an accumulated difference between the flow rates generated by the pumps P1, P2 during the second measurement phase.

It is seen that the functions F1 and F2 compute the actual stroke volumes as long as the set values are chosen such that (n1·n4)≠(n2·n3). Basically, this means that the pumps P1, P2 are operated at different combinations of frequencies during the first and second measurement phases. In this context, setting the frequency of pump P1 in the second measurement phase equal to the frequency of pump P2 in the first measurement phase, and setting the frequency of pump P2 in the second measurement phase equal to the frequency of pump P1 in the first measurement phase, result in a different combination of frequencies. It lies within the reach of the skilled person to optimize the combinations of frequencies to suppress the impact of computation errors, e.g. to avoid that the denominator (n1·n4−n2·n3) is close to zero.

It is also seen that the actual stroke volumes S1, S2 may be computed if the speed of one pump is set to zero in the first measurement phase, and optionally if the speed of the other the pump is set to zero in the second measurement phase, i.e. by setting n1=0 (and possibly n4=0) and/or by setting n2=0 (and possibly n3=0). However, it is preferable that the pumps P1, P2 are operated at non-zero speeds in both phases since this will increase the first and second time periods t1, t2, and thereby increase the accuracy of the computed actual stroke volumes S1, S2.

The foregoing embodiments presume that the pumps P1, P2 are set to fixed speeds during the respective measurement phase. However, the skilled person appreciates that it is equally possible to allow the speeds of the pumps P1, P2 to vary during the measurement phases, as long as the control unit 30 operates or implements a function that relates the actual stroke volumes to the varying pump speeds, the time periods t1, t2 and the volumes V1, V2.

In certain embodiments, the start and end levels for the first and second measurement phases are not predefined, but are chosen more or less arbitrarily while the fluid level is reciprocated in the chamber 26. Such an embodiment presumes that the volumes (V1 and V2) between such arbitrarily chosen start and end levels are known to the control unit 30. For example, if the chamber 26 has a known cross-section area, the control unit 30 may calculate the volumes V1, V2 between the respective start and end levels. In a variant, the control unit 30 stores a table of volumes between different levels in the calibration chamber 26 and uses this table to obtain the volumes V1, V2.

It is conceivable that the control unit 30 may repeat steps 102-106 a number of times and calculates the actual stroke volumes S1, S2 as an average of the actual stroke volumes that are generated for the respective pump P1, P2 by the repeated execution of step 106.

It is to be understood that the actual stroke volumes S1, S2 that are obtained in step 106 are estimations and are affected by measurement and calculation errors. The accuracy of the calculated stroke volumes S1, S2 may be affected by differences between the set speeds n1, n2, n3, n4 and the actual speeds of the pumps P1, P2, systematic errors in the volumes V1, V2 caused by manufacturing tolerances of the chamber 26 and inaccuracies in the placement of the level detector 28, as well as timing errors when measuring the times t1, t2. The impact of differences between the set speeds n1, n2, n3, n4 and the actual speeds of the pumps P1, P2 may be suppressed by feedback control of the speed of the pumps P1, P2 based on the output of a respective pulse generator (not shown) in the pumps P1, P2, as is well-known in the art. Such a pulse generator, which may be implemented as a conventional pulse encoder or tachometer, is associated with the respective pump P1, P2 to generate one or more pulses for each stroke volume that is displaced by the pump P1, P2. Systematic errors in the volumes V1, V2 and timing errors generally have a weak impact on the resulting UF rate. This can be shown by reverting to the numeric example given above, where the actual stroke volumes of the pumps in FIG. 1 are S1=3.838 and S2=3.762. Assume that the volume V between L1 and L2 is 20 ml and that timing errors in the level detector 28 causes the volume V to be underestimated by 0.015 ml in the filling phase (steps 102-103) and overestimated by 0.015 ml during the emptying phase (steps 104-105). Under this assumption, and using realistic values of the pump speeds (n1-n4), step 106 may calculate the actual stroke volumes to S1=3.833646 and S2=3.757653. This, in turn, will result in an actual UF rate of 501.2 ml/h, which is close to the desired value of 500 ml/h. It should be noted that the measurement error of 0.015 ml, corresponding to 0.075%, is merely given as an example and that significantly larger measurement errors may be acceptable in other implementations.

Figure 4:
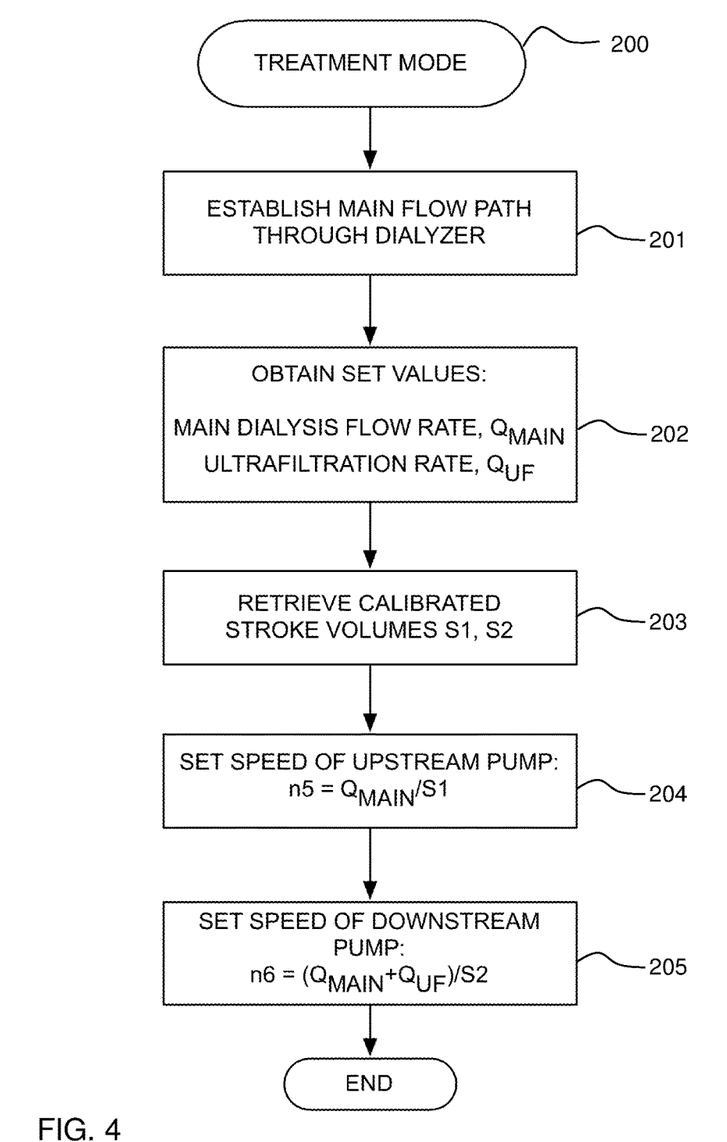
FIG. 4 is a flow chart of a treatment mode executed by the control unit in the system of FIG. 1.
Figure 5:
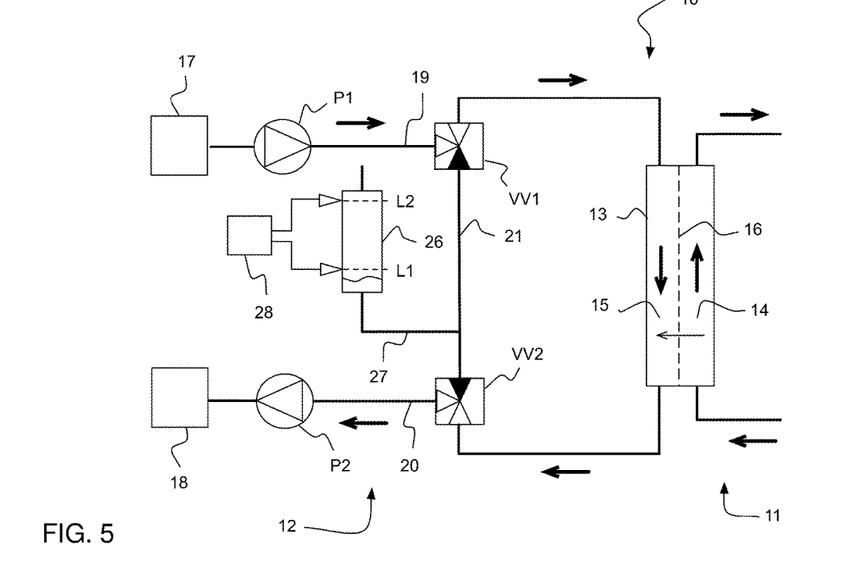
FIG. 5 illustrate the operation of the system in FIG. 1 during the treatment mode in FIG. 4.

As noted above, the system 10 in FIG. 1 is also operable in a treatment mode, in which a desired UF rate is achieved in the dialyzer 13. An embodiment of the treatment mode 200 is represented in the flow chart of FIG. 4 and will be discussed below with further reference to FIG. 5. In a first step 201, the valves VV1, VV2 are controlled to establish a flow path ("main flow path") from the pump P1 via the dialysis fluid side 15 of the dialyzer 13 to the pump P2, such that all of the fresh dialysis fluid from source 17 is pumped through the dialyzer 13 and that all of the spent dialysis fluid is pumped from the dialyzer 13 to the receptacle 18. In the example of FIG. 5, the valves VV1, VV2 are controlled to establish fluid communication between the inlet and outlet conduits 19, 20 and the dialyzer 13, while closing off fluid communication between the inlet and outlet conduits 19, 20 and the bypass conduit 21. In step 202, set values are obtained for the flow rate of dialysis fluid into the dialyzer 13, denoted main flow rate and designated by $Q_{MAIN}$, and the ultrafiltration rate, designated by $Q_{UF}$. The set values $Q_{MAIN}$, $Q_{UF}$ may be pre-stored in and retrieved from the memory 33 or they may be acquired in real time via a user interface (not shown) associated with the control unit 30 or the dialysis apparatus. In step 203, the actual stroke volumes S1, S2 that were determined by the control unit 30 in the calibration mode (FIG. 2) are retrieved from the memory 33. In step 204, the speed n5 of the upstream pump P1 is calculated and set to achieve the main dialysis flow $Q_{MAIN}$, given the actual stroke volume S1, i.e. $n5=Q_{MAIN}/S1$. In step 205, the speed n6 of the downstream pump P2 is calculated and set to achieve a difference of flow rates between the pumps P1, P2 equal to the ultrafiltration rate $Q_{UF}$, given the actual stroke volume S2, i.e. n6=$(Q_{MAIN}+Q_{UF})$/S2. As indicated by thick arrows in FIG. 5, dialysis fluid will be pumped through the dialysis fluid side 15 of the dialyzer 13, while blood is being pumped through the blood side 14 of the dialyzer 13. The difference in flow rates between the pumps P1, P2 draws ultrafiltrate from the blood into the dialysis fluid, as indicated by the horizontal arrow in the dialyzer 13 in FIG. 5.

It is to be understood that the set value $Q_{UF}$ may vary during a treatment, and the control unit 30 will control the speed n6 of the downstream pump P2 accordingly. The set value $Q_{MAIN}$ is typically held constant during a treatment, although it can certainly be varied during if desired.

In a variant, the set value $Q_{MAIN}$ instead represents the flow of dialysis fluid out of the dialyzer 13, and step 204 involves calculating and setting the speed n6 of the downstream pump P2 according to n6=$Q_{MAIN}$/S2. In this variant, step 205 involves calculating and setting the speed n5 of the pump P1 according to n5=$(Q_{MAIN}-Q_{UF})$/S1. In many dialysis systems, it is desirable to maintain a constant flow of dialysis fluid from the source 17, e.g. when the source 17 is configured to prepare the dialysis fluid by mixing of one or more concentrates with water. The complexity of such a source 17 may increase if the source 17 need to handle momentary changes in the amount of dialysis fluid to be output. In such dialysis systems, the embodiment in FIG. 5 may be preferable, where the UF rate is controlled by adjusting the speed of the downstream pump P2.

It is to be understood that the control unit 30 may be operated in the calibration mode at any time, e.g. at manufacture of a dialysis machine that include the dialysis fluid circuit, before start of a dialysis treatment, intermittently during a dialysis treatment, or after a completed dialysis treatment. Each calibration mode results in actual stroke volumes S1, S2 of the pumps P1, P2.

In the above-described embodiments, the actual stroke volumes S1, S2 for both pumps P1, P2 are calculated in the calibration mode and used in the treatment mode for controlling the UF rate. However, it is conceivable that the actual stroke volume for only one of the pumps P1, P2 may be calculated in the calibration mode, and that this calculated actual stroke volume is used together with the nominal stroke volume of the other pump for controlling the UF rate in the treatment mode.

Figure 6:
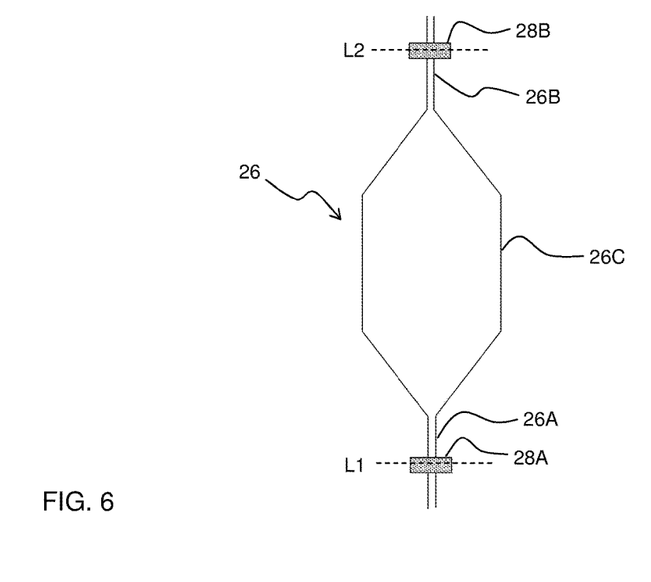
FIG. 6 is an elevated side view of a calibration chamber for use in the system of FIG. 1.

FIG. 6 illustrates a calibration chamber 26 which is designed with a well-defined volume V between two levels L1, L2. The calibration chamber 26 is designed as a pipette and has capillary tubes 26A, 26B connected to the top and bottom of a hollow bulb 26C. Level sensing elements 28A, 28B are arranged at the capillary tubes 26A, 26B to detect presence of fluid at the lower and upper levels L2, L2. The majority of the volume contained within the calibration chamber 26 between levels L1, L2 is defined within the bulb 26C. The chamber 26 in FIG. 6 may be installed in the system 10 of FIG. 1 by connecting the capillary tube 26A to the connecting conduit 27.

Figure 7:
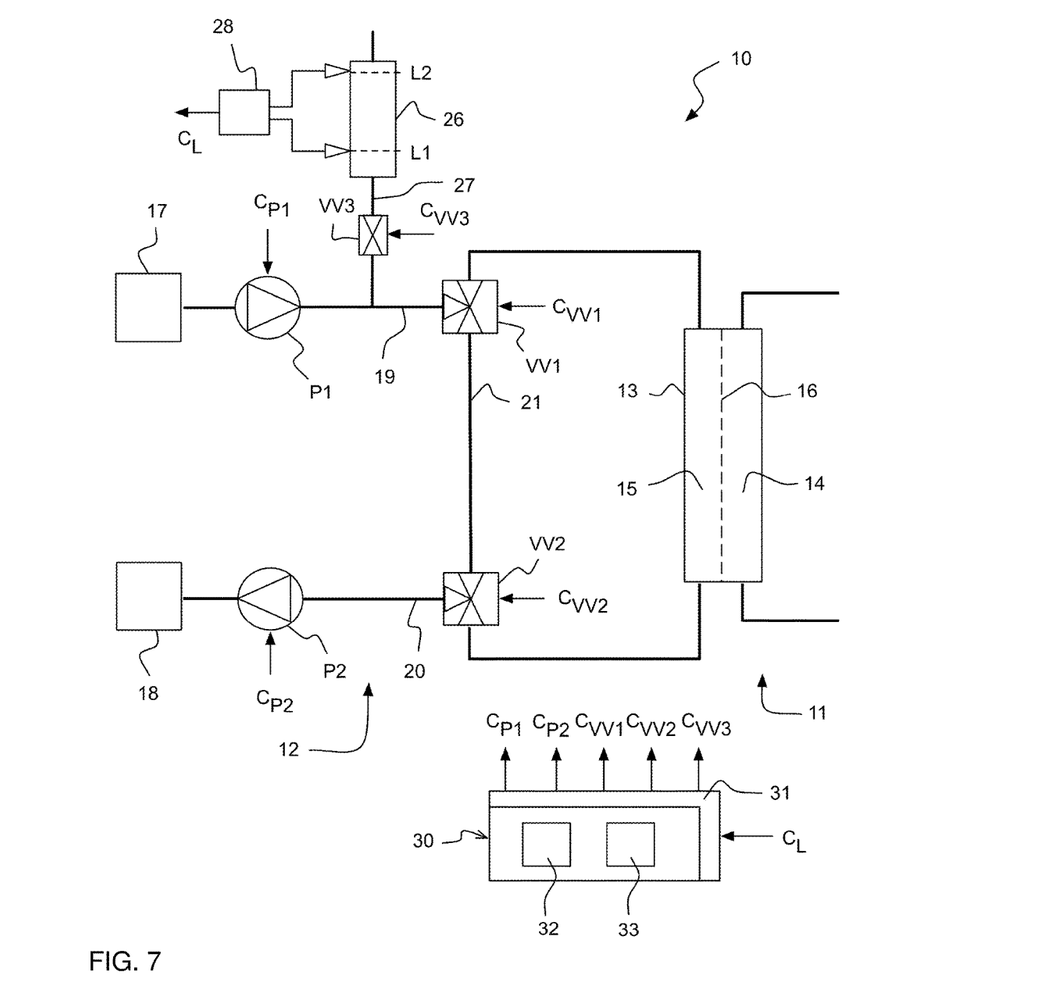
FIG. 7 is a block diagram of a system for ultrafiltration according to another embodiment.

FIG. 7 illustrates another embodiment of a system 10 for ultrafiltration. The system 10 in FIG. 7 differs from the system in FIG. 1 by the placement of the calibration chamber 26. The chamber 26 is arranged for fluid communication with the inlet conduit 19 between the upstream pump P1 and the first valve VV1 via a connecting conduit 27. An on/off valve VV3 is arranged in the connecting circuit 27 to selectively establish fluid communication between the chamber 26 and the inlet conduit 19. The control unit 30 is configured to generate a control signal $C_{VV3}$ for controlling the opening and closing of the valve VV3. The foregoing embodiments, variants and examples are equally applicable to the embodiment in FIG. 7, with the difference that the control unit 30 operates the valve VV3 to open the connecting conduit 27 when the bypass flow path is established in step 101 during the calibration mode 100, and operates the valve VV3 to close off the connecting conduit 27 when the main flow path is established in step 201 during the treatment mode 200. In variant (not shown), the chamber 26 is instead connected for fluid communication with the outlet conduit 20 between the second valve VV2 and the pump P2.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the system for ultrafiltration may include more than one upstream pump and/or more than one downstream pump. The actual stroke volumes for these pumps may be calculated as described herein, by establishing the bypass flow path between pairs of upstream and downstream pumps and performing steps 102-106 for each pair of upstream and downstream pumps.

The upstream and downstream pumps are volumetric pumps and may be implemented as either piston pumps or diaphragm (membrane) pumps. It is to be understood that the upstream and downstream pumps may have different nominal stroke volumes. It is also possible that the upstream and downstream pumps are of different designs or types.

The calibration chamber need not be a dedicated chamber but may instead be an existing chamber that serves another purpose in a dialysis apparatus, e.g. as part of a device for removing gas (e.g. carbon dioxide or air) from the dialysis fluid. Such an existing chamber may be intermittently switched into fluid communication with the bypass flow path between the pumps P1, P2 during the calibration mode.

In the foregoing description, the control unit 30 controls the UF rate exclusively by setting the difference in the flow rates between the upstream and downstream pumps, using the actual stroke volumes obtained in the calibration mode. In an alternative embodiment, the control unit 30 sets the flow rates of the upstream and downstream pumps equal, using the actual stroke volumes obtained in the calibration mode, and controls the UF rate by operating a dedicated UF pump ("filtration pump"), which is connected to the outlet conduit 20 between the downstream pump P2 and the dialyzer 13, as is well-known in the art and described in the Background section. It is also conceivable to configure the control unit 30 to set the UF rate by a combination of controlling a separate UF pump and controlling the difference in flow rates between the upstream and downstream pumps.

The invention claimed is:
1. A dialysis apparatus, comprising:
a dialyzer;
a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber;

a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid;

wherein the control unit is configured to, in a calibration mode, perform a first and second measurement procedure while operating the dialysis fluid distribution system to establish the bypass flow path;

wherein the first measurement procedure comprises:
controlling the first and second pumps to operate at a first combination of frequencies that results in a first flow rate difference between the flow rates generated by the first and second pumps, and
measuring, by the fluid level detector, a first time period corresponding to a first change in dialysis fluid level in the calibration chamber as a result of the first flow rate difference, the first change in dialysis fluid level corresponding to a first known volume in the calibration chamber;

wherein the second measurement procedure comprises:
controlling the first and second pumps to operate at a second combination of frequencies that differs from the first combination of frequencies and results in a second flow rate difference between the flow rates generated by the first and second pumps, and
measuring, by the fluid level detector, a second time period corresponding to a second change in dialysis fluid level in the calibration chamber as a result of the second flow rate difference, the second change in dialysis fluid level corresponding to a second known volume in the calibration chamber;

wherein the control unit is further configured to compute at least one of the stroke volumes of the first and second pumps as a function of the first and second combinations of frequencies, the first and second time periods, and the first and second known volumes; and wherein the function is obtained by solving a system of equations that equates the first known volume to an accumulated difference between the flow rates generated by the first and second pumps during the first time period, and that equates the second known volume to an accumulated difference between the flow rates generated by the first and second pumps during the second time period.

2. The dialysis apparatus of claim 1, wherein the control unit is further configured to, in the calibration mode, store the stroke volume(s) computed in the calibration mode in an electronic memory for subsequent retrieval by the control unit in a treatment mode.

3. The dialysis apparatus of claim 1, wherein the first and second pumps are positive displacement pumps, and wherein the flow rates of dialysis fluid generated by the first and second pumps are given by the respective frequency multiplied by the respective stroke volume.

4. The dialysis apparatus of claim 1, wherein the control unit is configured to set the first and second combinations of frequencies such that the first change is an increase in dialysis fluid level in the calibration chamber, and the second change is a decrease in dialysis fluid level in the calibration chamber.

5. The dialysis apparatus of claim 1, wherein the first change is from a first level to a second level in the calibration chamber, and the second change is from the second level to the first level in the calibration chamber.

6. The dialysis apparatus of claim 1, wherein the control unit is configured to, in the first measurement procedure, set the first and second pumps to fixed first and second frequencies, and, in the second measurement procedure, set the first and second pumps to fixed third and fourth frequencies.

7. The dialysis apparatus of claim 6, wherein the function is given by:

$$\begin{bmatrix} S1 \\ S2 \end{bmatrix} = \frac{1}{n1 \cdot n4 - n2 \cdot n3} \cdot \begin{bmatrix} n4 & -n2 \\ n3 & -n1 \end{bmatrix} \cdot \begin{bmatrix} V1/t1 \\ V2/t2 \end{bmatrix}$$

where S1 is the stroke volume of the first pump, S2 is the stroke volume of the second pump, n1 is the first frequency, n2 is the second frequency, n3 is the third frequency, n4 is the fourth frequency, V1 is the first known volume corresponding to the first change in dialysis fluid level, V2 is the second known volume corresponding to the second change in dialysis fluid level, t1 is the first time period, and t2 is the second time period, wherein V1 is positive for an increase in dialysis fluid level and negative for a decrease in dialysis fluid level and V2 is positive for a decrease in dialysis fluid level and negative for an increase in dialysis fluid level.

8. The dialysis apparatus of claim 1, wherein each of the first and second pumps is one of a diaphragm pump and a piston pump.

9. The dialysis apparatus of claim 1, wherein the control unit is further operable in a treatment mode to operate the dialysis fluid distribution system to establish the main flow path and control the frequencies of the first and second pumps, based on the stroke volume(s) computed in the calibration mode, so as to achieve a predefined ultrafiltration rate in the dialyzer.

10. The dialysis apparatus of claim 9, wherein the predefined ultrafiltration rate is achieved by setting the frequencies of the first and second pumps to achieve a predefined difference between the flow rates generated by the first and second pumps.

11. The dialysis apparatus of claim 9, wherein the control unit is configured to, in the treatment mode, receive a set value for the flow rate of one of the first and second pumps, and compute, by applying the corresponding stroke volume computed in the calibration mode, the frequency of said one of the first and second pumps to achieve the set value.

12. The dialysis apparatus of claim 11, wherein said one of the first and second pumps is the first pump.

13. The dialysis apparatus of claim 11, wherein the control unit is configured to, in the treatment mode, receive a set value for the ultrafiltration rate in the dialyzer, compute an ultrafiltration control flow rate for the other of the first and second pumps based on the set values for the flow rate and the ultrafiltration rate, and compute, by applying the corresponding stroke volume computed in the calibration mode, the frequency of said other of the first and second pumps to achieve the ultrafiltration control flow rate.

14. A method of calibrating a dialysis fluid distribution system that comprises first and second pumps which are connected upstream and downstream of a dialyzer to pump a dialysis fluid through the dialyzer, wherein the first and second pumps are configured to generate a respective flow rate by repeatedly discharging, at a respective frequency, a respective stroke volume of the dialysis fluid, said method comprising:
operating the dialysis fluid distribution system to establish a bypass flow path, which bypasses the dialyzer and extends from the first pump to the second pump in fluid communication with a calibration chamber;
controlling the first and second pumps to operate at a first combination of frequencies that results in a first flow rate difference between the flow rates generated by the first and second pumps;
measuring a first time period corresponding to a first change in dialysis fluid level in the calibration chamber as a result of the first flow rate difference, the first change in dialysis fluid level corresponding to a first known volume in the calibration chamber;
controlling the first and second pumps to operate at a second combination of frequencies that differs from the first combination of frequencies and results in a second flow rate difference between the flow rates generated by the first and second pumps;
measuring a second time period corresponding to a second change in dialysis fluid level in the calibration chamber as a result of the second flow rate difference, the second change in dialysis fluid level corresponding to a second known volume in the calibration chamber; and
computing at least one of the stroke volumes of the first and second pumps as a function of the first and second combinations of frequencies, the first and second time periods, and the first and second known volumes, wherein the function is obtained by solving a system of equations that equates the first known volume to an accumulated difference between the flow rates generated by the first and second pumps during the first time period, and that equates the second known volume to an accumulated difference between the flow rates generated by the first and second pumps during the second time period.

15. A computer-readable medium comprising program instructions which, when executed by a processing unit, are adapted to carry out the method of claim 14.

16. A control unit for a dialysis fluid distribution system arranged in a dialysis apparatus to pump a dialysis fluid through a dialyzer, wherein the dialysis fluid distribution system comprises first and second pumps which are connected upstream and downstream of the dialyzer to pump a dialysis fluid through the dialyzer, and are configured to generate a respective flow rate by repeatedly discharging, at a respective frequency, a respective stroke volume of the dialysis fluid, said control unit comprising:
a signal communication interface for connection to the dialysis fluid distribution system; and
a signal processor which is configured to, via the signal communication interface:
operate the dialysis fluid distribution system to establish a bypass flow path, which bypasses the dialyzer and extends from the first pump to the second pump in fluid communication with a calibration chamber;
control the first and second pumps to operate at a first combination of frequencies that results in a first flow rate difference between the flow rates generated by the first and second pumps;
measure, by a fluid level detector for sensing a level of dialysis fluid in the calibration chamber, a first time period corresponding to a first change in dialysis fluid level in the calibration chamber as a result of the first flow rate difference, the first change in dialysis fluid level corresponding to a first known volume in the calibration chamber;
control the first and second pumps to operate at a second combination of frequencies that differs from the first combination of frequencies and results in a second flow rate difference between the flow rates generated by the first and second pumps; and
measure, by the fluid level detector, a second time period corresponding to a second change in dialysis fluid level in the calibration chamber as a result of the second flow rate difference, the second change in dialysis fluid level corresponding to a second known volume in the calibration chamber; and
wherein the signal processor is further configured to compute at least one of the stroke volumes of the first and second pumps as a function of the first and second combinations of frequencies, the first and second time periods, and the first and second known volumes.

17. A control unit for a dialysis fluid distribution system arranged in a dialysis apparatus to pump a dialysis fluid through a dialyzer, wherein the dialysis fluid distribution system comprises first and second pumps which are connected upstream and downstream of the dialyzer to pump a dialysis fluid through the dialyzer, wherein the first and second pumps are configured to generate a respective flow rate by repeatedly discharging, at a respective frequency, a respective stroke volume of the dialysis fluid, said control unit comprising:
means for operating the dialysis fluid distribution system to establish a bypass flow path, which bypasses the dialyzer and extends from the first pump to the second pump in fluid communication with a calibration chamber;
means for controlling the first and second pumps to operate at a first combination of frequencies that results in a first flow rate difference between the flow rates generated by the first and second pumps;
means for measuring a first time period corresponding to a first change in dialysis fluid level in the calibration chamber as a result of the first flow rate difference, the first change in dialysis fluid level corresponding to a first known volume in the calibration chamber;
means for controlling the first and second pumps to operate at a second combination of frequencies that differs from the first combination of frequencies and results in a second flow rate difference between the flow rates generated by the first and second pumps;
means for measuring a second time period corresponding to a second change in dialysis fluid level in the calibration chamber as a result of the second flow rate difference, the second change in dialysis fluid level corresponding to a second known volume in the calibration chamber; and
means for computing at least one of the stroke volumes of the first and second pumps as a function of the first and second combinations of frequencies, the first and second time periods, and the first and second known volumes.

18. A dialysis apparatus, comprising:
a dialyzer;
a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber;

a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid;

wherein the control unit is configured to, in a calibration mode, perform a first and second measurement procedure while operating the dialysis fluid distribution system to establish the bypass flow path;

wherein the first measurement procedure comprises:
controlling the first and second pumps to operate at a first combination of frequencies that results in a first flow rate difference between the flow rates generated by the first and second pumps, and
measuring, by the fluid level detector, a first time period corresponding to a first change in dialysis fluid level in the calibration chamber as a result of the first flow rate difference, the first change in dialysis fluid level corresponding to a first known volume in the calibration chamber;

wherein the second measurement procedure comprises:
controlling the first and second pumps to operate at a second combination of frequencies that differs from the first combination of frequencies and results in a second flow rate difference between the flow rates generated by the first and second pumps, and
measuring, by the fluid level detector, a second time period corresponding to a second change in dialysis fluid level in the calibration chamber as a result of the second flow rate difference, the second change in dialysis fluid level corresponding to a second known volume in the calibration chamber, wherein the control unit is further configured to compute at least one of the stroke volumes of the first and second pumps as a function of the first and second combinations of frequencies, the first and second time periods, and the first and second known volumes, and wherein the control unit is configured to set the first and second combinations of frequencies such that the first change is an increase in dialysis fluid level in the calibration chamber, and the second change is a decrease in dialysis fluid level in the calibration chamber.

19. A dialysis apparatus, comprising:
a dialyzer;
a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber;
a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid;

wherein the control unit is configured to, in a calibration mode, perform a first and second measurement procedure while operating the dialysis fluid distribution system to establish the bypass flow path;

wherein the first measurement procedure comprises:
controlling the first and second pumps to operate at a first combination of frequencies that results in a first flow rate difference between the flow rates generated by the first and second pumps, and
measuring, by the fluid level detector, a first time period corresponding to a first change in dialysis fluid level in the calibration chamber as a result of the first flow rate difference, the first change in dialysis fluid level corresponding to a first known volume in the calibration chamber;

wherein the second measurement procedure comprises:
controlling the first and second pumps to operate at a second combination of frequencies that differs from the first combination of frequencies and results in a second flow rate difference between the flow rates generated by the first and second pumps, and
measuring, by the fluid level detector, a second time period corresponding to a second change in dialysis fluid level in the calibration chamber as a result of the second flow rate difference, the second change in dialysis fluid level corresponding to a second known volume in the calibration chamber, wherein the control unit is further configured to compute at least one of the stroke volumes of the first and second pumps as a function of the first and second combinations of frequencies, the first and second time periods, and the first and second known volumes, and wherein the first change is from a first level to a second level in the calibration chamber, and the second change is from the second level to the first level in the calibration chamber.

20. A dialysis apparatus, comprising:
a dialyzer;
a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber;
a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid;

wherein the control unit is configured to, in a calibration mode, perform a first and second measurement procedure while operating the dialysis fluid distribution system to establish the bypass flow path;

wherein the first measurement procedure comprises:
controlling the first and second pumps to operate at a first combination of frequencies that results in a first flow rate difference between the flow rates generated by the first and second pumps, and measuring, by the fluid level detector, a first time period corresponding to a first change in dialysis fluid level in the calibration chamber as a result of the first flow rate difference, the first change in dialysis fluid level corresponding to a first known volume in the calibration chamber;

wherein the second measurement procedure comprises:
controlling the first and second pumps to operate at a second combination of frequencies that differs from the first combination of frequencies and results in a second flow rate difference between the flow rates generated by the first and second pumps, and measuring, by the fluid level detector, a second time period corresponding to a second change in dialysis fluid level in the calibration chamber as a result of the second flow rate difference, the second change in dialysis fluid level corresponding to a second known volume in the calibration chamber, wherein the control unit is further configured to compute at least one of the stroke volumes of the first and second pumps as a function of the first and second combinations of frequencies, the first and second time periods, and the first and second known volumes, and wherein the control unit is configured to, in the first measurement procedure, set the first and second pumps to fixed first and second frequencies, and, in the second measurement procedure, set the first and second pumps to fixed third and fourth frequencies.

21. A dialysis apparatus, comprising:
a dialyzer;
a dialysis fluid distribution system connected for fluid communication with the dialyzer and comprising a first pump, a second pump, a calibration chamber, and a fluid level detector for sensing a level of dialysis fluid in the calibration chamber, the dialysis fluid distribution system being operable to selectively establish a main flow path that extends from the first pump to the second pump via the dialyzer, and a bypass flow path that bypasses the dialyzer and extends from the first pump to the second pump in fluid communication with the calibration chamber;
a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid;

wherein the control unit is configured to, in a calibration mode, perform a first and second measurement procedure while operating the dialysis fluid distribution system to establish the bypass flow path;

wherein the first measurement procedure comprises:
controlling the first and second pumps to operate at a first combination of frequencies that results in a first flow rate difference between the flow rates generated by the first and second pumps, and measuring, by the fluid level detector, a first time period corresponding to a first change in dialysis fluid level in the calibration chamber as a result of the first flow rate difference, the first change in dialysis fluid level corresponding to a first known volume in the calibration chamber;

wherein the second measurement procedure comprises:
controlling the first and second pumps to operate at a second combination of frequencies that differs from the first combination of frequencies and results in a second flow rate difference between the flow rates generated by the first and second pumps, and measuring, by the fluid level detector, a second time period corresponding to a second change in dialysis fluid level in the calibration chamber as a result of the second flow rate difference, the second change in dialysis fluid level corresponding to a second known volume in the calibration chamber, wherein the control unit is further configured to compute at least one of the stroke volumes of the first and second pumps as a function of the first and second combinations of frequencies, the first and second time periods, and the first and second known volumes, wherein the control unit is further operable in a treatment mode to operate the dialysis fluid distribution system to establish the main flow path and control the frequencies of the first and second pumps, based on the stroke volume(s) computed in the calibration mode, so as to achieve a predefined ultrafiltration rate in the dialyzer, and wherein the control unit is configured to, in the treatment mode, receive a set value for the flow rate of one of the first and second pumps, and compute, by applying the corresponding stroke volume computed in the calibration mode, the frequency of said one of the first and second pumps to achieve the set value.

\* \* \* \* \*